(12) United States Patent
Tang et al.

(10) Patent No.: US 6,984,308 B2
(45) Date of Patent: Jan. 10, 2006

(54) ELECTROCHEMICAL ANALYSIS OF COENZYME $Q_{10}$ AND REDUCED COENZYME $Q_{10}$

(75) Inventors: Peter H. Tang, Cincinnati, OH (US);
Ton de Grauw, Cincinnati, OH (US);
Michael V. Miles, Cincinnati, OH (US)

(73) Assignee: Cincinnati Children's Hospital Research Foundation, Cincinnati, OH (US)

( * ) Notice: Subject to any disclaimer, the term of this patent is extended or adjusted under 35 U.S.C. 154(b) by 450 days.

(21) Appl. No.: 10/090,347

(22) Filed: Mar. 4, 2002

(65) Prior Publication Data

US 2002/0125193 A1  Sep. 12, 2002

Related U.S. Application Data

(60) Provisional application No. 60/273,684, filed on Mar. 6, 2001.

(51) Int. Cl.
*G01N 27/27* (2006.01)
*G01N 30/64* (2006.01)

(52) U.S. Cl. ...................... 205/787; 205/789; 73/61.58; 204/409

(58) Field of Classification Search .................. 422/70; 436/161; 73/61.58; 204/409, 411, 412; 205/775, 205/787, 789, 789.5
See application file for complete search history.

(56) References Cited

U.S. PATENT DOCUMENTS

| | | | |
|---|---|---|---|
| 4,511,659 A | | 4/1985 | Matson ....................... 436/150 |
| 4,552,013 A | * | 11/1985 | Matson ....................... 73/61.55 |
| 4,863,873 A | | 9/1989 | Matson ........................ 436/63 |
| 5,011,608 A | | 4/1991 | Damjanovic ................. 210/656 |
| 5,104,639 A | | 4/1992 | Matson ........................... 424/2 |
| 5,726,565 A | | 3/1998 | Uchiyama et al. ............ 324/94 |

OTHER PUBLICATIONS

"Electrochemical Cell Designs for Coulochem® Detectors" made by ESA, Inc.,.downloaded from www.esainc.com on May 27, 2004.*
Schieffer et al., "Precolumn Coulometric Celll for High-Performance Liquid Chromatography," Anal. Chem. 1981, 53, 126–127.*
Tang et al. "Simple and rapid HPLC method with coulometric detection of coenzyme Q10 in human plasma and CSF," Book of Abstracts, 219th ACS National Meeting, San Francisco, CA, Mar. 26–30, 2000.*
"Sulfur Cycle Lecture Outline", www.cas.muohio.edu/~mbi–ws/biogeochemicalcycles/Sulfur/sulcyclecout.htm, downloaded Nov. 16, 2004.*
"Chemical of the Week—Phosphoric Acid, H3PO4" scifun.chem.wisc.edu/CHEMWEEK?H3PO4/H3PO4.html, downloaded Nov. 16, 2004.*
"Diagram of the Sulfur Cycle", www.alken–murray.com/H2SREM7.HTM, downloaded Nov. 16, 2004, only p. 1 of 2.*
"Sulfur Cycle Lecture Outline", www.cas.muohio.edu/~mbi–ws/biogeochemicalcycles/Sulfur/sulcyclecout.htm, downloaded Nov. 16, 2004.*

(Continued)

*Primary Examiner*—Alex Noguerola
(74) *Attorney, Agent, or Firm*—Frost Brown Todd LLC

(57) ABSTRACT

This invention relates to an apparatus and method for the simultaneous and rapid determination of $CoQ_{10}$ and $CoQ_{10}H_2$ concentrations in human samples using HPLC-EC. The electrochemical reactions are monitored at electrodes that measure the current produced by the reduction of the hydroquinone group of $CoQ_{10}$ or by the oxidation of the hydroquinol group of $CoQ_{10}H_2$.

6 Claims, 10 Drawing Sheets

Schematic Diagram of HPLC-EC System

OTHER PUBLICATIONS

"Chemical of the Week—Phosphoric Acid, H3PO4" sci-fun.chem.wisc.edu/CHEMWEEK?H3PO4/H3PO4.html, downloaded Nov. 16, 2004.*

"Diagram of the Sulfur Cycle", www.alken–murray.ocm/H2SREM7.HTM, downloaded Nov. 16, 2004.*

Takada, M., Ikenoya, S., Yuzuriha, T., and Katayama, K. Simultaneous Determination of Reduced and Oxidized Ubiquinones. *Method.Enzy.* 1984, 105: 147–155.

Lang, J.K., Gohil, K., and Packer, L. Simultaneous Determination of Tocopherols, Ubiquinols, and Ubiquinones in Blood, Plasma, Tissue Homogenates, and Subcellular Fractions. *Anal. Biochem.* 1986, 157: 106–116.

Edlund, P.O. Determination of CoEnzyme $Q_{10}$, C– Tocopherol and Cholesterol in Biological Samples by Coupled–Column Liquid Chromatography with Coulometric and Ultraviolet Detection. *J.Chrom.* 1988, 425: 87–97.

Okamoto, T., Fukunaga, Y., Ida, Y., and Kishi, T. Determination of Reduced and Total Ubiquinones in Biological Materials by Liquid Chromatography with Electrochemical Detection, *J. Chrom B,* 1988, 430: 11–19.

Grossi, G., Bargossi, A.M., Fiorella, P.L., and Piazzi, S. Improved High–Performance Liquid Chromatographic Method for the Determination of Coenzyme Q10 in Plasma. *J.Chrom.* 1992, 593: 217–226.

Wakabayashi, H., Yamato, S., Nakajima, M., and Shimada, K. Simultaneous Determination of Oxidized and Reduced Coenzyme $Q_{10}$ and C–Tocopherol in Biological samples by High Performance Liquid Chromatography with Platinum Catalyst Reduction and Electrochemical Detection. *Biol. Pharm. Bull.* 1994, 17:997–1002.

Finckh, B., Kontush, A., Commentz, J., Hubner, C., Burdelski, M., and Kohlschutter, A. Monitoring of Ubiquinol–10, Ubiquinone–10, Carotenoids, and Tocopherols in Neonatal Plasma Microsamples Using High–Performance Liquid Chromatography wit Coulometric Electrochemical Detection. *Anal. Biochem.* 1995, 232: 210–216.

Lagendijk, J., Ubbink, J.B., Delport, R., Hayward, W. J., and Human J.A. Measurement of the Ratio Between the Reduced and Oxidized forms of $CoQ_{10}$ in Human Plasma as a Possible Marker of Oxidative Stress. *J.Lip.Res.* 1996, 37:67–75.

Yamashita S., and Yamamoto, Y., Simultaneous Detection of Ubiquinol and Uniquinone in Human Plasma as a Marker of Oxidative Stress. *Anal Biochem* 1997, 250: 66–73.

Kaikkonen, J., Nyyssonen, K., and Salonen, J.T. Measurement and Stability of Plasma Reduced, Oxidized and Total Coenzyme $Q_{10}$ in Humans, *Scan J. Clin Lab Invest.* 1999, 59: 457–466.

Wang, Q., Lee, B.L., and Ong, C.N.: Automated High–Performance Liquid Chromatographic Method with Pre–column Reduction for the Determination of Ubiquinol and Ubiquinone in Human Plasma. *J.Chrom. B.* 1999, 726: 297–302.

Tang, Peter H., Miles, Michael V., DeGrauw, Antonius, Steele, Paul E., Hershey, Andrew, Schroer, Laura, Chuck, Gail, Jones, Jeanne, and Pesce, Amadeo. Simple and Rapid HPLC Method with Coulometric Detection of Coenzyme $Q_{10}$ in Human Plasma and CSF. OASYS, Paper No. 387537.

Tang, Peter H., Miles, Michael V., DeGrauw, Antonius, Hershey, Andrew, and Pesce, Amadeo. HPLC Analysis of Reduced and Oxidized Coenzyme $Q_{10}$ in Human Plasma. Clinical Chemistry, 47:256–265.

* cited by examiner

ELECTROCHEMICAL ANALYSIS OF COENZYME $Q_{10}$ AND REDUCED COENZYME $Q_{10}$

This application is based on and claims priority from U.S. Provisional Patent Application Ser. No. 60/273,684, Peter H. Tang, Ton deGrauw, Michael V. Miles, filed Mar. 6, 2001.

FIELD OF INVENTION

The present invention relates to a method of electrochemical analysis of an aqueous solution containing materials having quinone and hydroquinone moieties. More particularly, the present invention relates to an electrochemical apparatus and method for the simultaneous measurements of coenzyme $Q_{10}$ and the reduced form of coenzyme $Q_{10}$ concentrations in human plasma samples.

BACKGROUND

Coenzyme $Q_{10}$ ($CoQ_{10}$), commonly known as ubiquinone-10, is present in blood and all body tissues in both reduced and oxidized forms. $CoQ_{10}$ has an important function in the mitochondrial electron transport chain (ETC) as an electron acceptor and as an electron donor. It is believed that the ETC is comprised of five multi-subunit enzyme complexes, in which $CoQ_{10}$ and cytochrome c act as shuttles between complex I and III and II and III. Complex I (NADH-ubiquinone oxidoreductase) transfers electron from NADH or NADPH to $CoQ_{10}$. Complex II (succinate-ubiquinone oxidoreductase) transfers electron from FADH or FMNH to $CoQ_{10}$. Complex III (ubiquinol-ferrocytochrome c oxidoreductase) transfers electron from reduced $CoQ_{10}$ ($CoQ_{10}H_2$) to cytochrome c. In addition, $CoQ_{10}H_2$ is one of the antioxidants that protect cells against lipid peroxidation. In the circulation, $CoQ_{10}$ is mainly carried by lipoproteins, where it is predominantly present in the reduced form. The $CoQ_{10}H_2$ in low density lipoprotein (LDL) is, however, easily oxidized to $CoQ_{10}$. In fact, $CoQ_{10}H_2$ is the first antioxidant to be depleted when LDL is subjected to oxidative stress in vivo. It has been postulated that $CoQ_{10}H_2$ prevents the initiation and/or the propagation of lipid peroxidation in plasma lipoproteins and biological membranes. The antioxidative activity of $CoQ_{10}H_2$ depends not only on its concentration but also on its redox status. Recent reports have suggested the percentage of $CoQ_{10}H_2$ in total plasma concentration of $CoQ_{10}$ ($TQ_{10}$) may be lower in patients with atherosclerosis, hyperlipidemia and coronary artery disease, and may be a useful biomarker of oxidative stress. Thus, the measurement of $CoQ_{10}H_2$ and $CoQ_{10}$ is of primary importance for clinical diagnosis.

Previous $CoQ_{10}H_2$ studies have encountered the problem of $CoQ_{10}H_2$ stability during sample handling, storage, and processing [1, 2, 3, 4, 5, 6, 7]. These studies indicate that $CoQ_{10}H_2$ is unstable in blood, plasma, and hexane extracts at room temperature. Subsequently, the $CoQ_{10}H_2:TQ_{10}$ ratio changes considerably within an hour after the blood sample has been obtained. The lability of $CoQ_{10}H_2$ is due to the hydroquinone moiety which is sensitive to oxygen, and at room temperature, it spontaneously oxidizes to $CoQ_{10}$ at a rate of ~2 nM per min. This problem is very obvious in many studies which have reported wide variability in the $CoQ_{10}H_2:TQ_{10}$ ratio in biological fluids [1, 2, 3, 4, 5, 6, 7]. It is believed that sample preparation has a profound effect on the redox status of $CoQ_{10}$ and that utmost care is required to ensure reliable estimates of the $CoQ_{10}H_2:TQ_{10}$ ratio. Recently, investigators have recommended that each plasma sample be thawed individually, extracted, and analyzed as a continuous process to minimize $CoQ_{10}H_2$ oxidation [8, 9, 10]. This is obviously very impractical for analyzing significant numbers of clinical specimens.

Several in-line post-column reduction methods of $CoQ_{10}$ to $CoQ_{10}H_2$ have also been reported for simultaneous measurements by electrochemical detection [3, 4]. The complex instrumentation and techniques used in those reports limit their practical value.

In earlier studies, biological fluid samples were converted into either $CoQ_{10}$ using an oxidizing reagent such as hydrogen peroxide or ferric chloride, or converted into $CoQ_{10}H_2$ using a reducing agent such as sodium tetrahydroborate or sodium dithionite (Table 1). In practice, however, since $CoQ_{10}H_2$ is easily oxidized when exposed to air, $CoQ_{10}H_2$ is susceptible to pre-analytical degradation and analytical error.

Therefore, we developed a simple and rapid procedure using an isocratic HPLC-EC method for simultaneous determination of $CoQ_{10}$ and $CoQ_{10}H_2$ in human samples. An electrochemical (EC) detector is preferred for detection of $CoQ_{10}H_2$ due to its high sensitivity. The electrochemical reactions are monitored at electrodes that measure the current produced by the reduction of the quinone group of $CoQ_{10}$ or by the oxidation of the hydroquinone group of $CoQ_{10}H_2$ (FIG. 1). This method may be used to investigate conditions by which the $CoQ_{10}H_2:TQ_{10}$ ratio can be reliably measured.

SUMMARY OF THE INVENTION

The present invention relates to an electrochemical detection apparatus and method for electrochemically determining the concentration of quinones and hydroquinones, such as $CoQ_{10}$ and $CoQ_{10}H_2$, in biological fluids. The detection method is sufficiently sensitive to permit the fluid sample to be as small as 100 μL.

The apparatus comprises a coulometric guard cell, which operates in an oxidative mode at about +700 mV or higher. This is arranged in series with an analytical cell that is placed after the guard cell. The analytical cell consists essentially of a series of at least two coulometric electrodes. The first electrode operates in a reductive mode at about −650 mV or lower. The second electrode operates in an oxidative mode at a potential that simultaneously detects and coulometrically measures electrochemically reversible materials in the sample solution. The operating potential for this second electrode is generally about +500 mV or higher. The guard cell and analytical cell are arranged so as to define collectively at least one flow channel for the sample solution to pass through. For many applications, a liquid chromatographic column is placed before the coulometric guard cell in order to achieve time-spaced separation of materials.

The sample itself comprises a mixture of electrochemically reversible materials, such as quinones and hydroquinones, contained in an aqueous solution. The aqueous solutions include, but are not limited to, water, juices, wine, milk, and aqueous pharmaceutical aqueous formulations. More particularly, the sample solution comprises a mixture of $CoQ_{10}$ and $CoQ_{10}H_2$ in heparinized human plasma which is diluted with 1-propanol. Although the present invention is primarily applicable to testing biological fluids such as plasma, serum, urine, CSF, breast milk, amniotic fluid, and blood, it may also be used to analyze solid matrices such as tissues, cell lysate and solid pharmaceutical formulations.

The method for simultaneous analysis a mixture of electrochemically reversible materials comprises dissolving the materials in a solution of 1-propanol. Once dissolved, the materials are passed through a liquid chromatographic column for achieving time-spaced separation of the materials eluted from the column. As these materials are eluted off the column, they are then oxidized as they pass through the coulometric guard cell. Once through the coulometric guard cell, the materials pass through an analytical cell consisting essentially of a series of at least two coulometric electrodes, wherein the first electrode operates in a reductive mode and the second electrode operates in an oxidative mode at a potential so as to detect and coulometrically measure electrochemically reversible materials in said sample. These coulometric cells are arranged in series to define collectively at least one flow channel for the sample solution.

An in-line pre-column reduction cell may also be placed between the injection port and the analytical column. This permits transformation of $CoQ_{10}$ into $CoQ_{10}H_2$, and vice versa. The yield of electrochemical reduction is approximately 99%.

DETAILED DESCRIPTION OF THE INVENTION

This invention relates to an apparatus for electrochemically analyzing an aqueous sample solution comprising electrochemically reversible materials in solution. In its broadest sense, electrochemically reversible materials are those which can be oxidized and/or reduced by the transfer of electrons. There may also be the transfer of protons ($H^+$) as well in order to form a chemically neutral species as the final product of the electron transfer reaction. Generally, the apparatus comprises an HPLC instrument, which includes a solvent delivery module (pump), an injector, inline filters, guard column and an analytical HPLC column for separation of the materials. In addition, immediately preceding the analytical column is at least one coulometric guard cell that can be used to oxidize or reduce the electrochemically active species. Following the analytical column is a series of in-line electrochemical cells for reduction and/or oxidation as well as analysis of the electrochemically active species. The coulometric guard cell preceding the analytical column and the series of post-column in-line electrochemical cells define collectively at least one flow channel for the sample solution.

The following methods are used to prepare the necessary standards:

Materials $CoQ_9$ and $CoQ_{10}$ are obtained from Sigma, St. Louis, Mo. HPLC grade methanol, ethanol, 1-propanol, 2-propanol and hexane are obtained from Fisher, and used without further purification. Sodium acetate and analytical grade acetic acid are also obtained from Fisher.

Preparation of Standard Solutions

The preparation work is carried out under a dim light to avoid photochemical decomposition of $CoQ_{10}$ and $CoQ_9$. To prepare a 5 ug/ml of a $CoQ_{10}$ working solution, 10 mg of $CoQ_{10}$ are dissolved in 10 mL of hexane and diluted to 100 mL with 1-propanol. The solution is thoroughly vortexed until dissolution is complete. A working solution is then prepared by diluting with 1-propanol to 5 ug/mL. The concentration of the working solution is then calculated by reading the absorbance at the spectrophotometer (275 nm, 1 cm light path quartz cuvette using epsilon=14,200). A series of calibration and control solutions is then prepared with the appropriate volume of 1-propanol to have final concentrations of 10, 100, 500, 1000, 2000, and 4000 ng/mL for $CoQ_{10}$ calibration solution, and the control solutions have final concentrations of 75, 750, and 1500 ng/mL $CoQ_{10}$. The $CoQ_9$ is chosen as an internal standard. To prepare a $CoQ_9$ solution, 2 mg of $CoQ_9$ are dissolved in 100 mL of 1-propanol. The $CoQ_9$ solution is thoroughly vortexed until dissolution is complete. A working solution of $CoQ_9$ is then prepared by diluting with 1-propanol to a concentration of 2 ug/mL. All the solutions are stored in 1.8 ml polypropylene tubes (Sarstedt, Newton, N.C., USA) at –20° C. and used throughout the study.

HPLC-EC System

Figure 1:
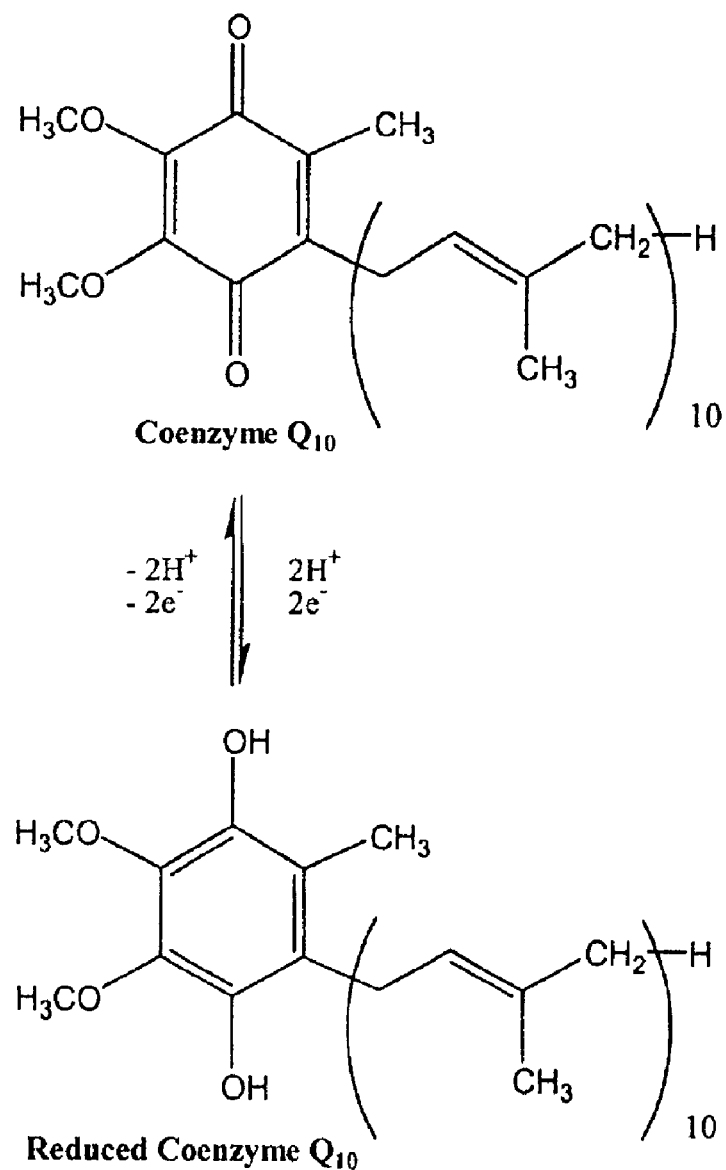
FIG. 1 shows the electrochemical reactivity of $CoQ_{10}H_2$ and $CoQ_{10}$.
Figure 2:
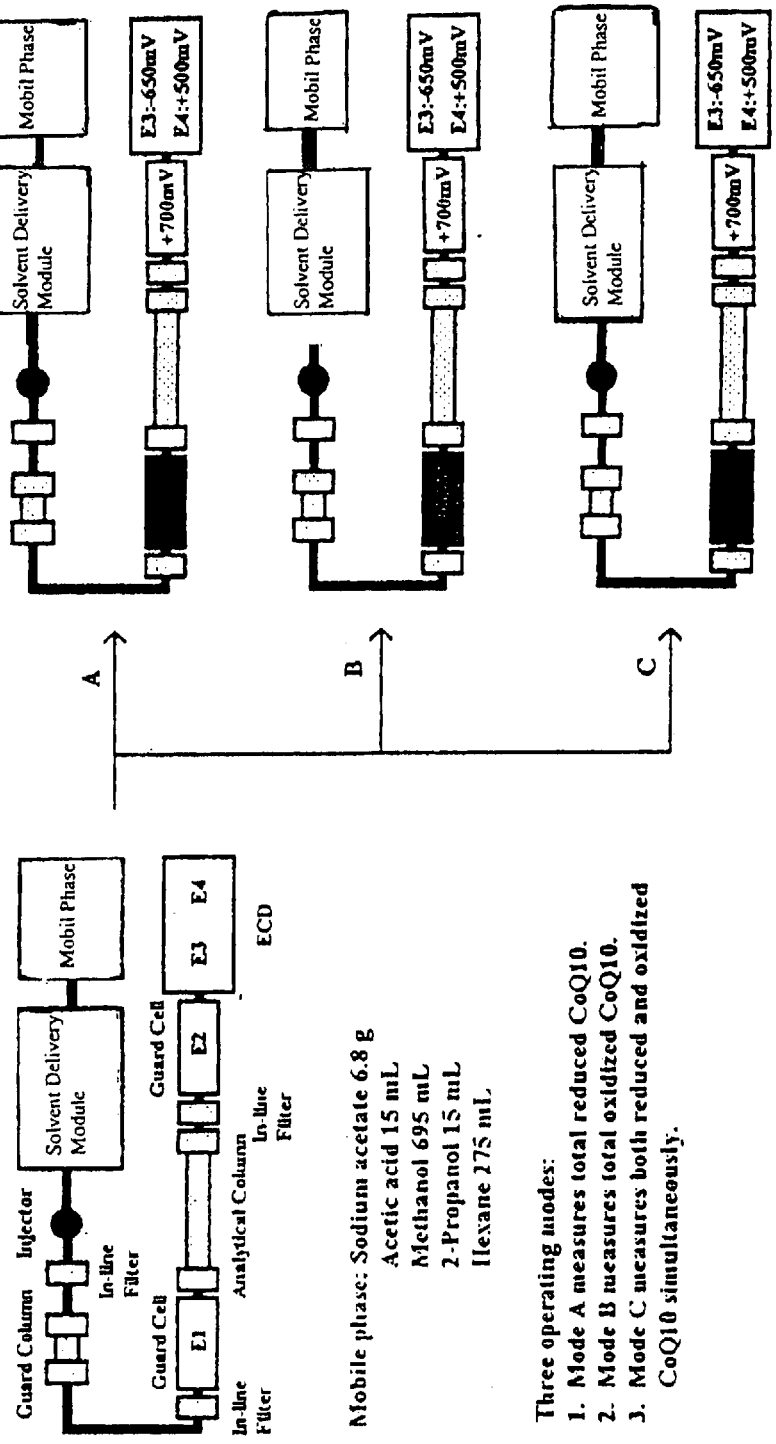
FIG. 2 is a schematic diagram of the HPLC-EC system. This system can be operated in three different modes as described in the present invention.

The HPLC-EC system is depicted in FIG. 2. For chromatography with coulometric analyses, the HPLC system consists of an ESA Model 582 Solvent Delivery Module (Bedford, Mass.) equipped with a double plunger reciprocating pump, an AS3000 variable-loop autosampler (Thermo Separation Products, Freemont, Calif., USA), an analytical column, an ESA CouloChem II Model 5200A electrochemical detector, and a Dell Pentium II 350 Mz computer/controller with ChromQuest software (Thermo Separation Products). The system also comprises two coulometric guard cells (E1 and E2, pre- and post-column, with respect to the analytical column, see FIG. 2) and an analytical cell, E3 and E4. There are also two in-line filters, wherein one in-line filter is placed before the guard cell E1 and the second in-line filter is placed between the analytical column and the guard cell (E2).

The analytical column used is a reverse-phase Microsorb-MV column (5 μm, 4.6 mm×15 cm). A reverse phase C 18 guard column (5-μm, 10×4.6 mm) is used to protect the analytical column. The analytical column temperature is at room temperature. The AS3000 injector is set at needle height of 1.5 mm and injection volume of 20 μl for each sample. The cooler temperature of the autosampler is at 0–4° C.

Each guard cell (E1 and E2) is a single coulometric cell (ESA Model 5020). The guard cells are installed before and after the analytical column (FIG. 2). The analytical cell (E3 and E4, ESA Model 5010) is connected in series to the postcolumn guard cell E2. The analytical cell consists of a series of two coulometric electrodes. The first electrode is operated in the reduction mode (about −650 mV or lower) for reduction of $CoQ_{10}$ and he second electrode is operated in the oxidation mode (about +500 mV or higher) for detection of $CoQ_{10}H_2$.

The mobile phase for the isocratic elution of $CoQ_{10}$ is prepared as follows: sodium acetate trihydrate (6.8 g), 15 mL of glacial acetic acid and 15 mL of 2-propanol are added to 695 ml of methanol and 275 ml of hexane. Mobile phase is filtered by 0.2 μm pore-sized, 47 mm nylon filter or analogous filter. Mobile phase has a pH value of 6. The flow rate is 1.0 mL/min.

Operation of Coulometric System

This system can be operated at three different modes for three different purposes: 1) precolumn reduction mode for measuring total $CoQ_{10}H_2$; 2) precolumn oxidation mode for measuring total $CoQ_{10}$; and 3) precolumn off mode for simultaneous determination of $CoQ_{10}H_2$ and $CoQ_{10}$.

In order to determine the optimal applied-voltage for EC detection, a hydrodynamic voltammogram is obtained by analyzing a solution of $CoQ_{10}$(4000 ng/mL) at different voltage settings. Anodic currents and cathodic currents reach maximum responses at applied voltages of +500 mV and −600 mV, respectively. Hence, the detection potential is maintained at +500 mV or higher vs. the hydrogen/palladium reference electrode.

For measuring total $CoQ_{10}H_2$, the precolumn guard cell is operated in the reduction mode (−800 mV or lower) in order to transform $CoQ_{10}$ to $CoQ_{10}H_2$. The reduction mode is also used to establish a calibration curve of $CoQ_{10}H_2$.

For measuring total $CoQ_{10}$, the precolumn guard cell is operated in the oxidation mode (+700 mV or higher) in order to oxidize $CoQ_{10}H_2$ to $CoQ_{10}$.

For measuring $CoQ_{10}H_2$ and $CoQ_{10}$ simultaneously, the precolumn guard cell is operated in the off mode (no current flows into the guard cell). The postcolumn guard cell is operated at oxidation mode (+700 mV or higher) to oxidize any electrochemically active elutes.

Sample Handling and Processing

Use of Heparin as an Anticoagulant for Blood Collection

According to the present invention, venous blood is collected into a VACUTAINER containing heparin as anticoagulant and mixed gently by inversion 5–6 times. At this point the blood-heparin tube is securely capped, and is then placed in ice and/or kept in refrigeration prior to processing. The blood-heparin tube should be processed within 4 hours. Blood samples should not be collected in tubes containing metal chelators, such as ethylenediaminetetraacetic acid (EDTA). The blood-heparin tube is subject to centrifugation at an appropriate speed such as 3000 rpm for 10 minutes at 4° C. Heparinized plasma is separated from red blood cells and placed in a capped polypropylene tube and immediately stored at −75° C. or below until analysis.

Extraction of $CoQ_{10}H_2$ and $CoQ_{10}$

Each frozen sample is thawed at room temperature, and 100 μl of this sample is placed in a 1.5-ml capped polypropylene tube containing 50 μl of internal standard solution ($CoQ_9$, 2 μg/mL in 1-propanol). All the tubes are kept in an ice-bath. This is mixed with 850 μl of cold 1-propanol. The tubes are vortexed for 2 minutes on a mechanical vortexer and centrifuged for 10 min at 0–4° C. The resulting supernatant is separated from the precipitate and transferred to an autosampler glass vial. The sample vial is immediately placed in the autosampler tray at 0–4° C. A batch of up to 20 samples can be extracted and processed at the same time. An aliquot of 20 μl of 1-propanol extract from a vial is injected immediately onto an automated HPLC. Twenty samples can be analyzed sequentially, within 4 hours. If an error has occurred in the system, these sample vials can be resealed and immediately restored at −75° C. or below for further investigation.

Analysis of $CoQ_{10}$ and $CoQ_{10}H_2$

Quantitation of $CoQ_{10}$ and $CoQ_{10}H_2$

Figure 3:
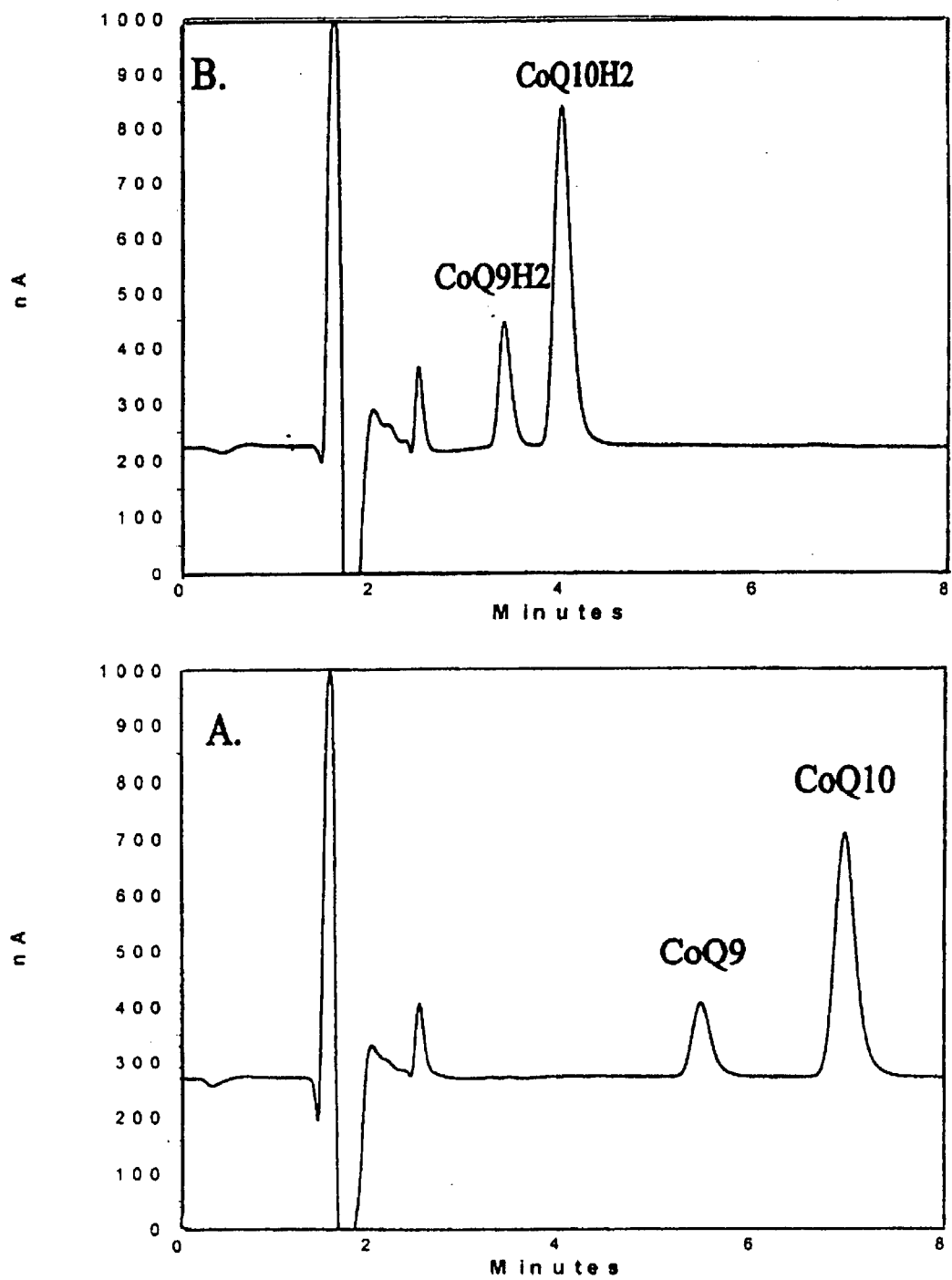
FIG. 3A is a chromatogram showing two oxidation peaks for standards of $CoQ_{10}$ and $CoQ_9$ at ~5.6 and ~6.9 min, respectively.
FIG. 3B is a chromatogram showing two oxidation peaks for standards of $CoQ_9H_2$ and $CoQ_{10}H_2$ at ~3.6 and ~4.0 min, respectively. Pre-column reduction mode was operated to transform $CoQ_{10}$ and $CoQ_9$ to $CoQ_{10}H_2$ and $CoQ_9H_2$, respectively.
Figure 4:
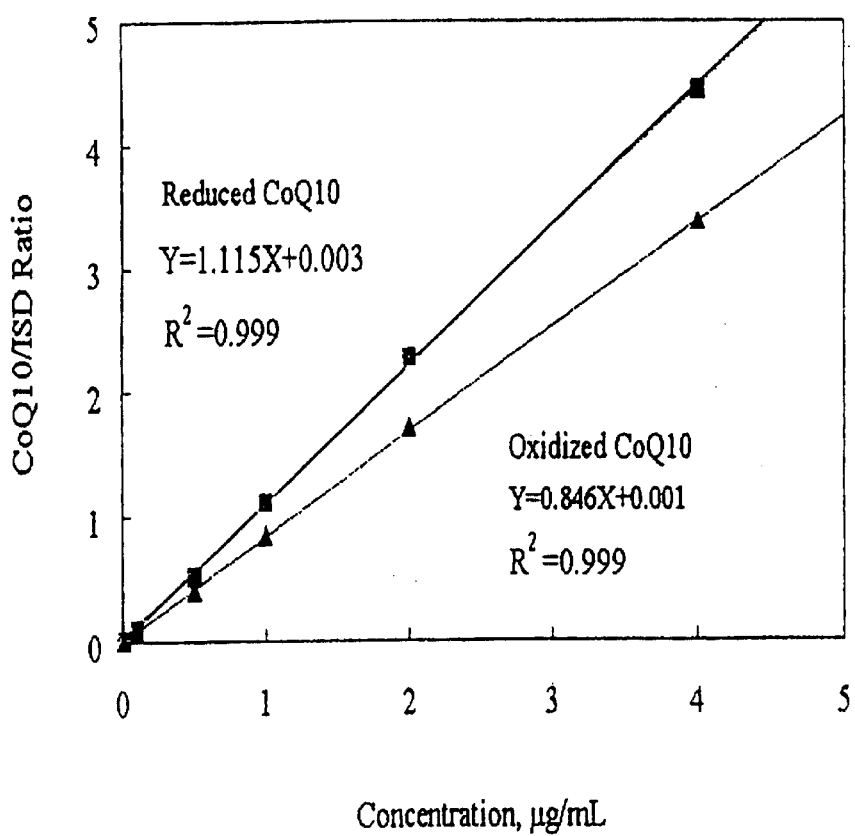
FIG. 4 shows plots of calibration curves for $CoQ_{10}$ and $CoQ_{10}H_2$. Standards of $CoQ_{10}$ were dissolved in 1-propanol.

Standard solutions of $CoQ_{10}$ are prepared as described above. Coulometric analysis and subsequent measurements of current responses are performed as described above. Two oxidation peaks are observed for $CoQ_9$ and $CoQ_{10}$ at approximately 5.6 min. and 6.9 min, respectively (FIG. 3). Peak height measurements for each calibration curve are obtained by using the ChromQuest software. The peak height ratios of $CoQ_{10}/CoQ_9$ are used to obtain least squares linear regression equations, which are used to calculate the $CoQ_{10}$ concentrations of the frozen control samples and patient samples. A linear response up to a concentration of 4 μg/mL of $CoQ_{10}$ is obtained when the peak height ratios are plotted versus $CoQ_{10}$ concentration (FIG. 4).

The same solutions of $CoQ_{10}$ used in the section describing Quantitation of $CoQ_{10}$ are reduced electrochemically for $CoQ_{10}H_2$ measurements as described above. Coulometric analysis and subsequent measurements of current responses are performed as described above. Two reduction peaks are observed for $CoQ_9H_2$ and $CoQ_{10}H_2$ at approximately 3.6 and 4.1 min, respectively (FIG. 3). The peak height measurements for each calibration are obtained by using the ChromQuest software. Peak height measurements of $CoQ_9$ obtained in the section of "Quantitation of $CoQ_{10}$" are used herein. The peak height ratios of $CoQ_{10}H_2/CoQ_9$ are used to obtain a least squares linear regression equation, which is then used to calculate the $CoQ_{10}H_2$ concentrations of the frozen control samples and patient samples. A linear response-up to a concentration of 4 μg/mL of $CoQ_{10}H_2$ is obtained when the peak height ratios are plotted versus $CoQ_{10}H_2$ concentration (FIG. 4).

Heparin Versus EDTA

Figure 5:
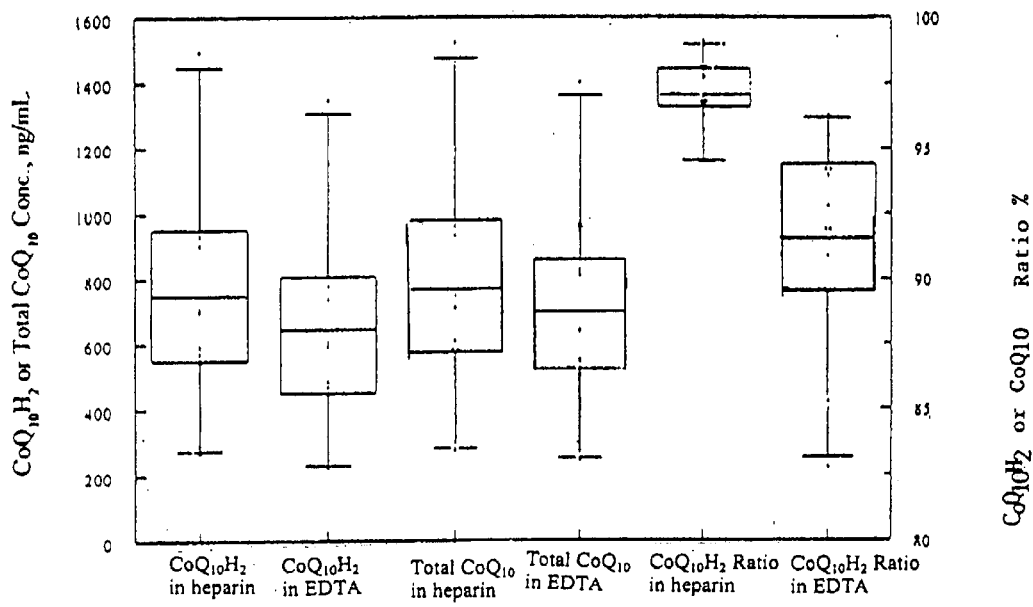
FIG. 5 is a graph comparing the effects of anticoagulant heparin and EDTA on $CoQ_{10}H_2$ stability among 13 blood samples collected in paired Vacutainer®s containing heparin and EDTA.

For $CoQ_{10}H_2$ analysis, many previous studies have wrongly used plasma samples anticoagulated with EDTA. The choice of anticoagulant has an effect on oxidation of $CoQ_{10}H_2$ (FIG. 5). Each patient's blood specimen is drawn into two paired VACUTAINERS containing heparin or EDTA. Although the time of sample handling and delivery may be varied from patient to patient, each pair of blood-containing tubes are handled and processed identically. The mean values of $CoQ_{10}H_2$ and $TQ_{10}$ from the heparinized plasma samples were 748(±346) and 770(±353) ng/mL, respectively, but somewhat poorer for those in EDTA-plasma with the mean values of 643(±321) and 696(±326) ng/mL, respectively. For the ratio of $CoQ_{10}H_2:TQ_{10}$ the mean values of heparinized plasma, 97.0(±1.4)%, were better than those in EDTA-plasma, 91.5(±4.4)%. These results clearly indicate that ratios and levels of $CoQ_{10}H_2$ and $TQ_{10}$ in heparinized plasma are consistently higher than in plasma anticoagulated with EDTA ($p<0.001$ for difference in paired samples).

When blood samples in vacutainers are opened and kept refrigerated, the $CoQ_{10}H_2:TQ_{10}$ ratios (n=30) in EDTA samples decreased by ~30% over 7 h, whereas the $CoQ_{10}H_2:TQ_{10}$ ratios in heparinized samples were stable over the same period with variation of less than 3% (median 0.949; range 0.927–0.970; n=30). There was as significant difference of $CoQ_{10}H_2:TQ_{10}$ ratios in heparin in EDTA (P=0.028). The observed findings therefore reflect the effect of air-exposure on EDTA samples during the blood sampling procedure. The results also indicate that delays, in processing and analyzing EDTA samples would result in lowered and variable $CoQ_{10}H_2:TQ_{10}$ ratios.

Using the presently described procedure, the $CoQ_{10}H_2:TQ_{10}$ ratio was >95% in the plasma specimens of normal volunteers. Heparin seems to possess antioxidant properties, but a previous study has shown that heparin has no direct antioxidant properties even at concentrations far higher than those usually used therapeutically. Thus, other mechanisms not strictly antioxidant-type may be involved in heparin-mediated protection on $CoQ_{10}H_2$. While not being bound by theory, it is thought that either heparin is interacting with a lipoprotein to enhance antioxidant protection perhaps through release of superoxide dismutase, or the chelation of metal ions by EDTA is limiting the activity of antioxidant metalloenzymes.

Figure 6:
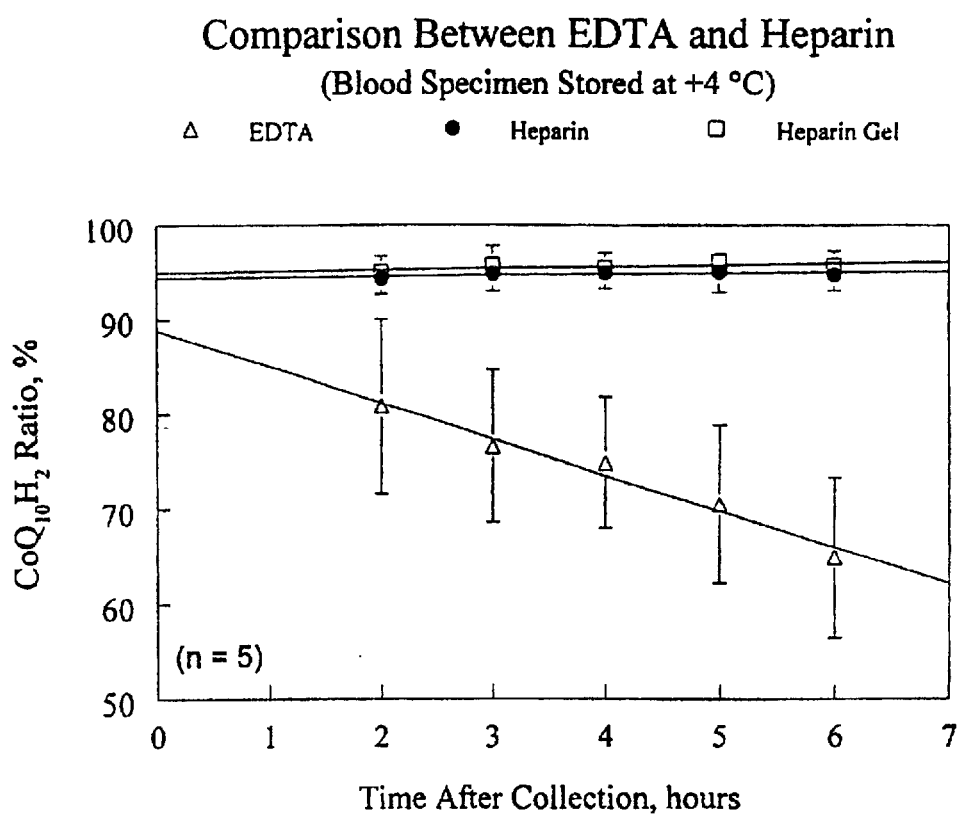
FIG. 6 is a graph comparing the effect of heparin and EDTA on $CoQ_{10}H_2$ in blood specimens over 6 hours. Blood specimens from 5 healthy volunteers were collected in paired VACUTAINERS containing heparin or EDTA and stored under refrigerated conditions.
Figure 7:
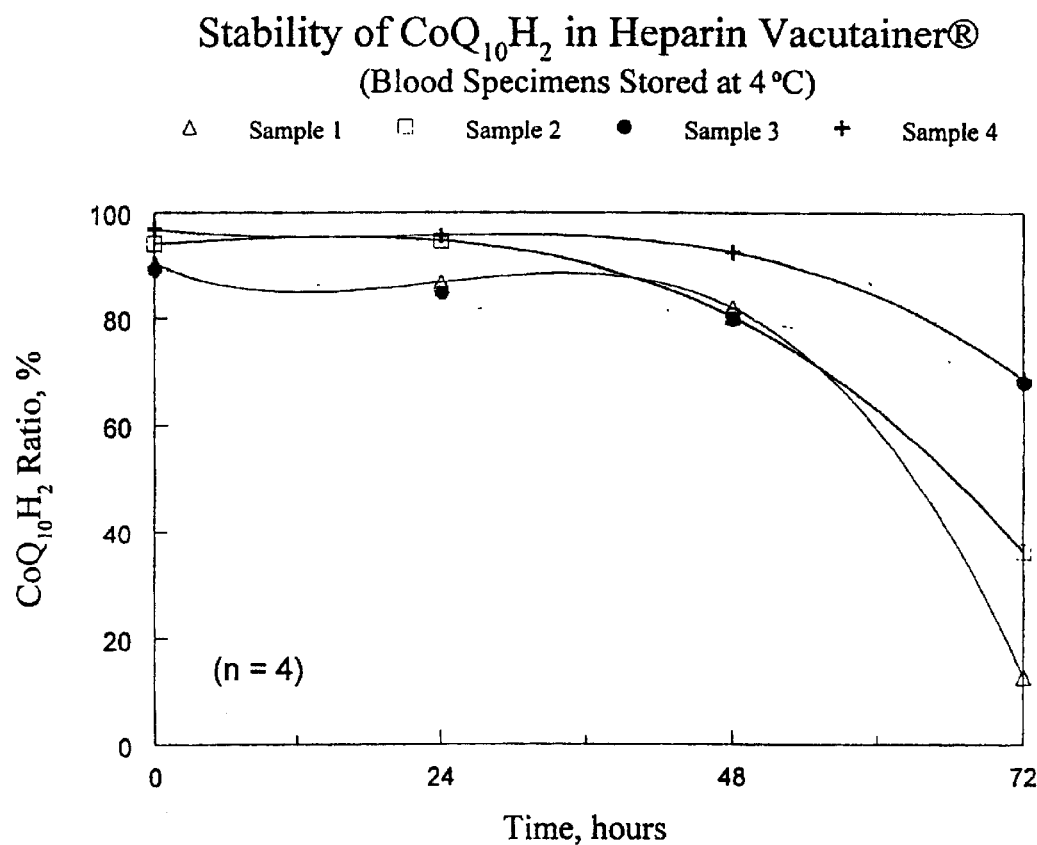
FIG. 7 is a stability profile of $CoQ_{10}H_2$ in blood specimens over a period of 72 hours.

Temperature Control $CoQ_{10}H_2$ is not stable and is oxidized in air at room temperature. $CoQ_{10}H_2$ is unstable in whole blood, plasma and n-propanol extract when EDTA is used as anticoagulant. EDTA-anticoagulated blood loses approximately 15% of $CoQ_{10}H_2$ within 4 hours when stored in refrigeration (4° C.), whereas only <1% loss of $CoQ_{10}H_2$ occurs in heparin-anticoagulated blood under the same conditions (FIG. 6). When fresh blood samples in closed heparin vacutainers are kept refrigerated, no significant difference in $CoQ_{10}H_2:TQ_{10}$ ratios was observed between samples stored for 0 h and 24 h (P=0.052). The median $CoQ_{10}H_2:TQ_{10}$ ratio stored for 24 h was 0.955 (range 0.923–0.972; n=8) in comparison to the initial value of 0.964 (range 0.935–0.978; n=8). The $CoQ_{10}H_2:TQ_{10}$ ratios decreased by ~6% after 48 h and by ~28% after 72 h. Storage of blood specimens in VACUTAINERS at +4° C. (in refrigeration prior to separation of plasma from blood cells can extend the stability of $CoQ_{10}H_2$ to 24 hours without a significant loss (<3%, See FIG. 7). Since blood $CoQ_{10}H_2$ in closed heparin VACUTAINERS kept refrigerated is stable for at least 24 hours, an overnight shipment of a blood sample on ice pack is acceptable for testing. When plasma is kept frozen at −75° C. or below, $CoQ_{10}H_2$ is stable for at least 6 months and the $CoQ_{10}H_2:TQ_{10}$ ratio does not change significantly during this period. Since measurements of $CoQ_{10}H_2$ from frozen samples is unfeasible, frozen samples must be thawed, extracted, and analyzed quickly to ensure minimal $CoQ_{10}H_2$ oxidation during the measurement process. Okamoto et al [10] reported the percentage of $CoQ_{10}H_2$ with respect to the $TQ_{10}$ was constant in plasma for one day when kept at 2° C. and −10° C. When extracted from plasma and prepared in ethanol solution, however, any $CoQ_{10}H_2$ in solution rapidly oxidized.

Figure 8:
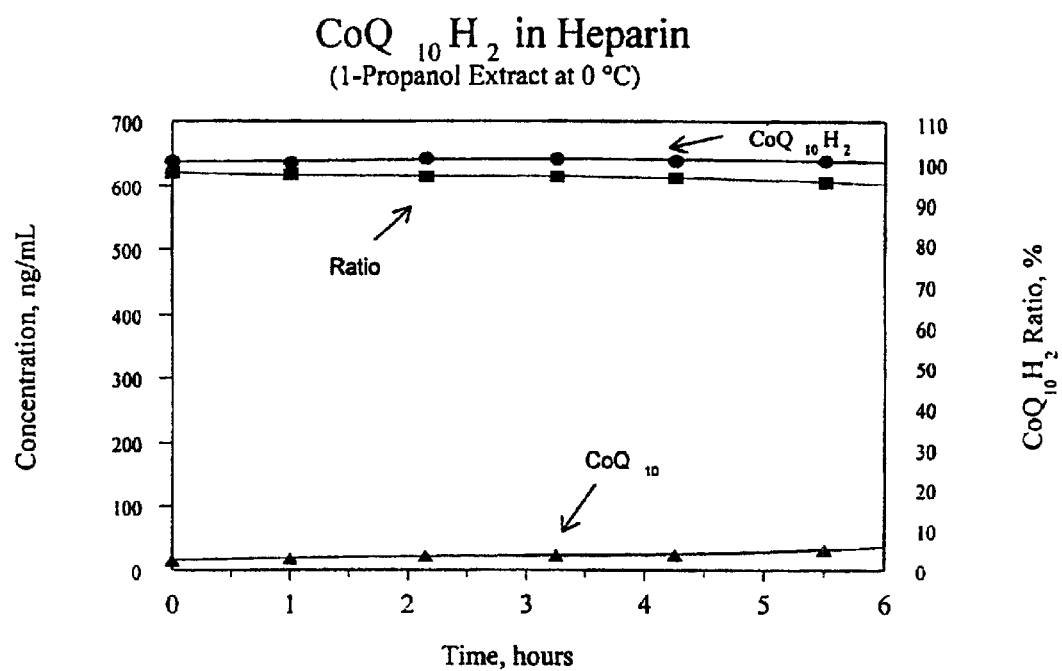
FIG. 8 is a graph showing the stability of $CoQ_{10}H_2$ in 1-propanol extract at 0–4° C.

An optimized HPLC system for measuring $CoQ_{10}H_2$ sequentially within 4 hours shows that 3.75% of $CoQ_{10}H_2$ in 1-propanol extract oxidizes in an hour (at a rate of ~2 nM/min) at room temperature, whereas, the loss of $CoQ_{10}H_2$ is only 1% in 5 hours when the temperature is set at 0–4° C. (FIG. 8).

Extraction with 1-Propanol

Using 1-propanol as an extracting solvent allows fast and simple sample processing. The procedure has been simplified to a single extraction and no evaporation process is needed. This allows for efficient sample handling. Extraction of $CoQ_{10}H_2$ and $CoQ_{10}$ from a variety of biological matrices is made facile with 1-propanol, because it can be mixed with water in any proportion. Additionally, $CoQ_{10}H_2$ and $CoQ_{10}$ have highest solubility in 1-propanol relative to other alcohols. Thus, 1-propanol is an effective extraction solvent (Table 2). The 1-propanol extract can be directly analyzed by the described HPLC-EC method. Furthermore, this procedure takes advantage of the use of $CoQ_9$ as an internal standard. Because the levels of $CoQ_9$ in human blood are negligible, it is desirable to spike control samples with this $CoQ_9$ to validate the extraction process.

High Specificity

Figure 9:
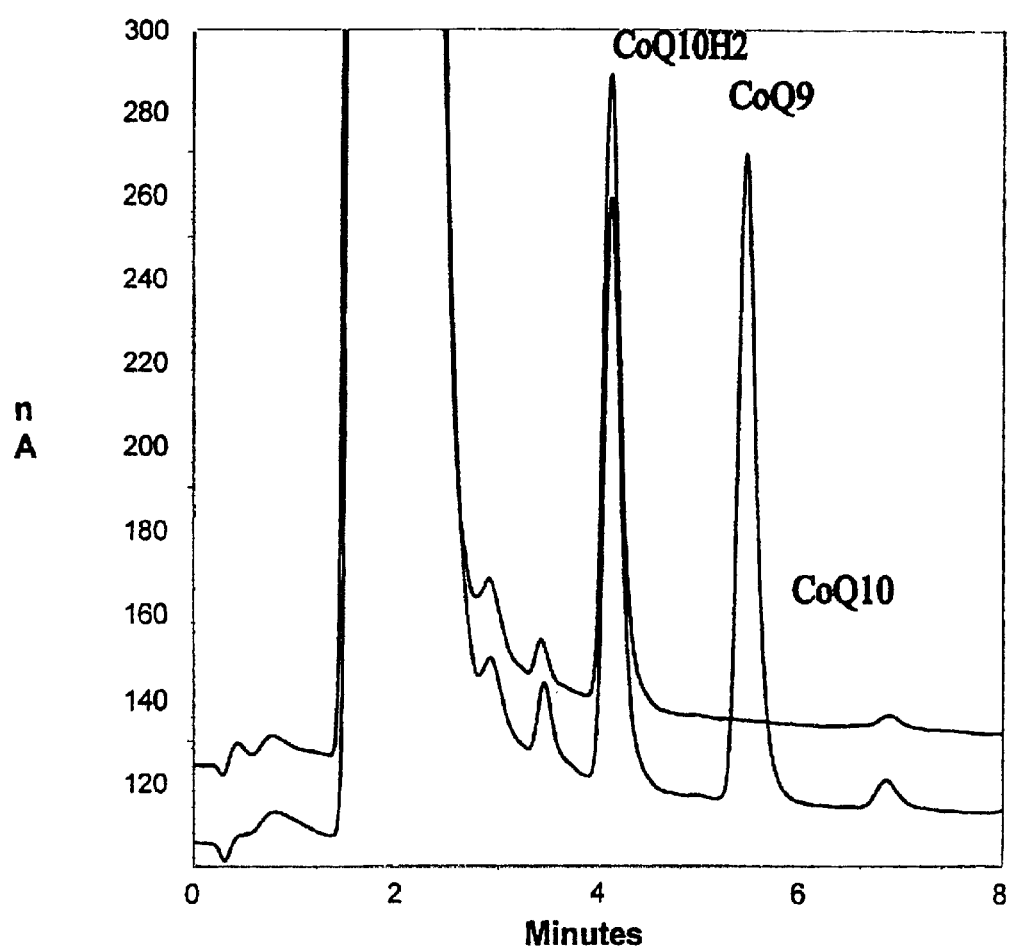
FIG. 9 shows a chromatograms of a patient's plasma extracts with and without $CoQ_9$ internal standard.
Figure 10:
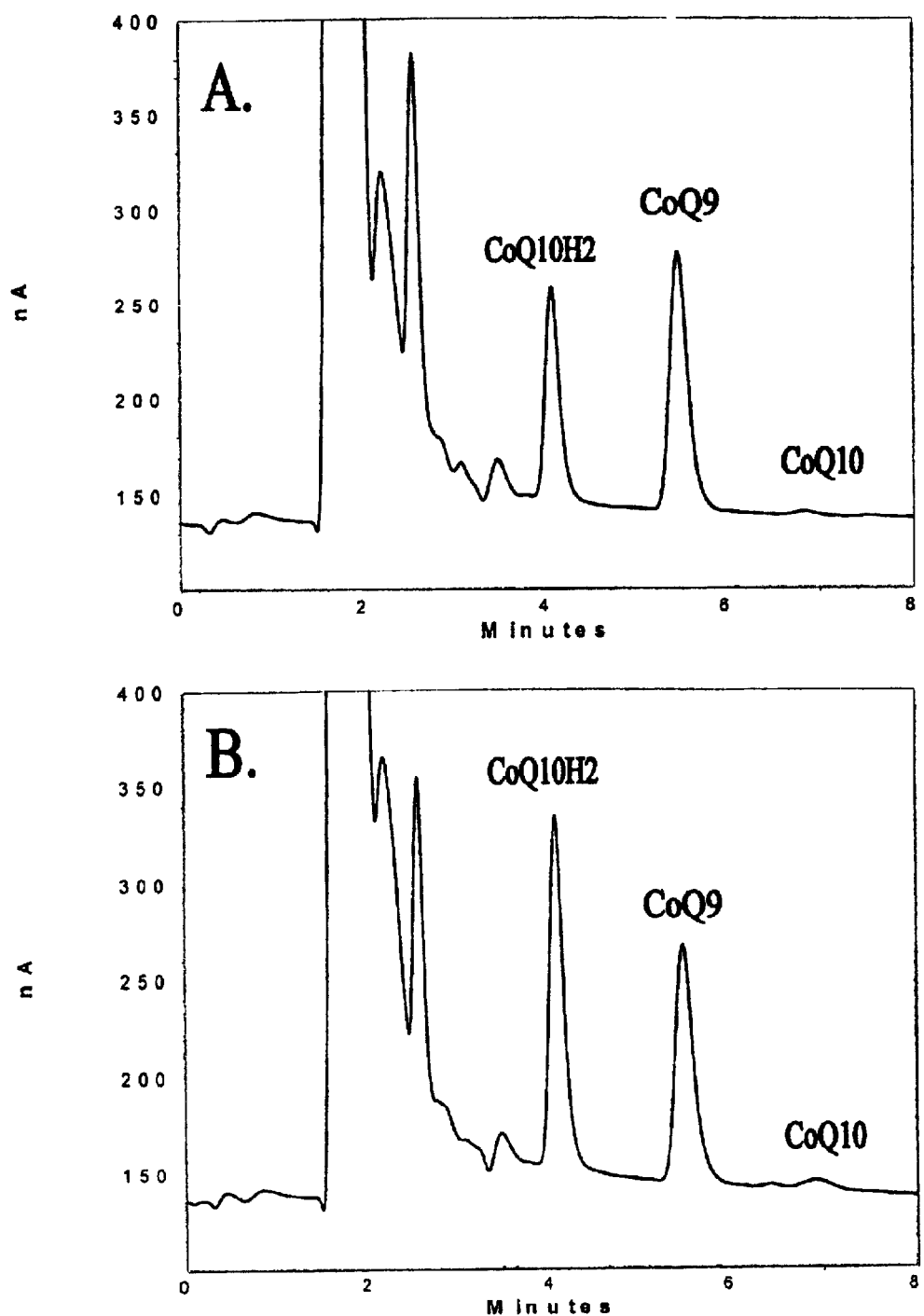
FIG. 10A shows a chromatogram of a patient's plasma extract before $CoQ_{10}$ supplementation.
FIG. 10B shows a chromatogram of a patient's plasma extract after $CoQ_{10}$ supplementation at a dosage of 60 mg/day.

Using a series of postcolumn guard cells and analytical cells operating within the stated oxidation and reduction potentials provides a high degree specificity to the detector system, and only those compounds capable of undergoing a reversible reduction-oxidation at the low potentials used are capable of being detected by the last electrode. Accordingly, as a result of a compromise involving the mobile phase composition, flow-rate and concentration of the supporting electrolyte, an excellent separation of an authentic mixture of $CoQ_9$, $CoQ_{10}$ and $CoQ_{10}H_2$ is obtained on a Microsorb-MV C18 column (15 cm×4.6 mm) using a mobile phase (pH ~6) containing 0.05 M sodium acetate at a flow-rate of 1.0 ml/min. A patient's sample was obtained according to the current method, wherein the retention times were 4.1 min for $CoQ_{10}H_2$, 5.6 min for $CoQ_9$ and 6.9 min for $CoQ_{10}$ (FIG. 9). The procedure described herein is useful for investigating the effect of $CoQ_{10}$ supplementation on patients with metabolic disorders (FIG. 10).

Reliable Measurement $CoQ_{10}H_2$ is generally obtained by chemical reduction of the commercially available $CoQ_{10}$. This requires a strong reducing agent such as sodium tetrahydroborate. The reduced form is unstable at room temperature and quickly becomes oxidized, so a fresh solution of $CoQ_{10}H_2$ must prepared daily. All these procedures are time consuming, labor-intensive, tedious and unsuitable for routine determinations. An alternative procedure using electrochemical reduction to obtain the reduced form relies on a coulometric detector which is able to provide more than 99% yield of the desired electrochemical reaction (Table 3) and thus providing a calibration curve for measuring the $CoQ_{10}H_2$ concentration.

The calibration curves for reduced $CoQ_{10}$ and oxidized $CoQ_{10}$ were linear (r=0.999) over the concentration range 10–4000 ng/ml. The detection limits of reduced $CoQ_{10}$ and oxidized $CoQ_{10}$ are about 5 ng/mL (S/N=3) (FIG. 4). This simplified 1-propanol extraction procedure is reproducible, allows for a recovery of $CoQ_{10}$, and allows for the assessment of the $CoQ_{10}H_2$ content from a standard concentration curve. Quantitative recovery of $CoQ_{10}$ (100%) using 1-propanol solvent has been obtained. The inter-day and intra-day assay variations (CVs) are less than 10% over a range 10–4,000 ng/mL (Table 4).

Time Requirement

The chromatography run time for each specimen is typically less than 10 minutes (FIG. 9). The total time required for a complete sample analysis is less than 30 minutes. This method allows at least 40 samples to be analyzed in an 8 hour working day, and 24 samples could be completed for overnight analysis.

REFERENCES

1. Takada, M., Ikenoya, S. Yuzuriha T., and Katayama, K. Simultaneous Determination of Reduced and Oxidized Ubiquinones. *Methods Enzymol*, 1984, 105: 147–155.

2. Lang, J. K., Gohil, K. and Packer, L. Simultaneous Determination of Tocopherols, Ubiquinols, and Ubiquinones in Blood, Plasma, Tissue Homogenates, and Subcellular Fractions. *Anal. Biochem.* 1986, 157: 106–116.
3. Edlund, P. O. Determination of Coenzyme $Q_{10}$, alpha-Tocopherol and Cholesterol in Biological Samples by Coupled-Column Liquid Chromatography with Coulometric and Ultraviolet Detection. *J Chrom.* 1988, 425: 87–97.
4. Okamoto, T., Fukunaga, Y., Ida, Y., and Kishi, T. Determination of Reduced and Total Ubiquinones in Biological Materials by Liquid Chromatography with Electrochemical Detection. *J Chrom B,* 1988, 430: 11–19.
5. Grossi, G., Bargossi, A. M., Fiorella, P. L., and Piazzi, S. Improved High-Performance Liquid Chromatographic Method for the Determination of Coenzyme Q10 in Plasma. *J Chrom.* 1992. 593:217–226.
6. Wakabayashi, H., Yamato, S., Nakajima, M., and Shimada, K. Simultaneous Determination of Oxidized and Reduced Coenzyme Q and alpha-Tocopherol in Biological samples by High Performance Liquid Chromatography with Platinum Catalyst Reduction and Electrochemical Detection. *Biol. Pharm. Bull.* 1994, 17: 997–1002.
7. Finckh, B., Kontush, A., Commentz, J., Hubner, C., Burdelski. M., and Kohlschutter, A. Monitoring of Ubiquinol-10, Ubiquinone-10, Carotenoids, and Tocopherols in Neonatal Plasma Microsamples Using High-Performance Liquid Chromatography with Coulometric Electrochemical Detection. *Anal. Biochem.* 1995. 232: 210–216.
8. Lagendijk, J., Ubbink. J. B. Delport, R., Hayward W. J., and Human J. A. Measurement of the Ratio Between the Reduced and Oxidized forms of CoQ10 in Human Plasma as a Possible Marker of Oxidative stress. *J Lip. Res.* 1996,37: 67–75.
9. Yamashita S., and Yamamoto, Y., Simultaneous Detection of Ubiquinol and Ubiquinone in Human Plasma as a Marker of Oxidative Stress. *Anal Biochem* 1997, 250: 66–73.
10. Kaikkonen, J., Nyyssonen, K., and Salonen, J. T. Measurement and Stability of Plasma Reduced, Oxidized and Total Coenzyme $Q_{10}$ in Humans. *Scan J Clin Lab. Invest.* 1999, 59: 457–466.
11. Wang, Q., Lee, B. L., and Ong, C. N.: Automated High-Performance Liquid Chromatographic Method with Pre-column Reduction for the Determination of Ubiquinol and Ubiquinone in Human Plasma. *J Chrom. B,* 1999. 726: 297–302.
12. Tang, Peter H., Miles, Michael V., DeGrauw, Antonius, Steele, Paul E., Hershey, Andrew, Schroer, Laura, Chuck, Gail, Jones, Jeanne, and Pesce, Amadeo. Simple and Rapid HPLC Method with Coulometric Detection of Coenzyme $Q_{10}$ in Human Plasma and CSF. OASYS, Paper No. 387537.
13. b Tang, Peter H., Miles, Michael V., DeGrauw, Antonius, Hershey, Andrew, and Pesce, Amadeo. HPLC Analysis of Reduced and Oxidized Coenzyme Q10 in Human Plasma. *Clin. Chem.,* 2001, 47:256–265.
14. Tang, P. H., Miles, M. V., Steele, P., deGrauw, A., Chuck, G., Schroer, L., and Pesce, A. Anticoagulant Effects on Plasma Coenzyme $Q_{10}$ Estimated by HPLC with Coulometric Detection. *Clin. Chem. Acta,* 2002, 318:127–131.

What is claimed is:

1. A method for simultaneously analyzing an aqueous mixture of quinones and hydroquinones in a biological fluid comprising the steps of:
    a) passing said mixture through a liquid chromatographic column for achieving time-spaced separation of the quinones and hydroquinones eluted from the column;
    b) oxidizing said hydroquinones by passing them through a coulometric guard cell having a voltage of at least about +700 mV; and
    c) passing said quinones and oxidized hydroquinones through an analytical cell consisting essentially of a series of at least two coulometric electrodes, wherein the first electrode operates in a reductive mode at about −650 mV and the second electrode mixture;

said at least two coulometric electrodes being arranged in series and defining collectively at least one flow channel for said mixture.

2. The method of claim 1 wherein the biological fluid is selected from the group consisting of plasma, serum, urine, CSF, amniotic fluid and blood.

3. The method of claim 2 wherein said aqueous mixture comprises a mixture of $CoQ_{10}$ and $CoQ_{10}H_2$ in a biological fluid.

4. The method of claim 3 wherein said biological fluid is heparinized human plasma.

5. The method of claim 4 wherein the aqueous mixture is diluted with 1-propanol.

6. The method of claim 1 further comprising using Coenzyme $Q_9$ as an internal standard.

* * * * *

UNITED STATES PATENT AND TRADEMARK OFFICE
CERTIFICATE OF CORRECTION

PATENT NO.    : 6,984,308 B2
DATED         : January 10, 2006
INVENTOR(S)   : Tang et al.

It is certified that error appears in the above-identified patent and that said Letters Patent is hereby corrected as shown below:

Column 10,
Line 28, claim 1, part c should read:
-- c) passing said quinones and oxidized hydroquinones through an analytical cell consisting essentially of a series of at least two coulometric electrodes, wherein the first electrode operates in a reductive mode at about -650 mV and the second electrode operates in an oxidative mode at about +500 mV, so as to detect and coulometrically measure electrochemically reversible quinones and oxidized hydroquinones in said mixture; --.

Signed and Sealed this

Sixth Day of June, 2006

JON W. DUDAS
*Director of the United States Patent and Trademark Office*